(12) United States Patent
Durkin et al.

(10) Patent No.: US 6,678,541 B1
(45) Date of Patent: Jan. 13, 2004

(54) OPTICAL FIBER PROBE AND METHODS FOR MEASURING OPTICAL PROPERTIES

(75) Inventors: Anthony J. Durkin, Watertown, MA (US); Marwood Ediger, Vienna, VA (US); L. Stephanie Matchette, Silver Spring, MD (US)

(73) Assignee: The Governmemt of the United States of America, Washinton D.C.

( * ) Notice: Subject to any disclaimer, the term of this patent is extended or adjusted under 35 U.S.C. 154(b) by 0 days.

(21) Appl. No.: 09/428,832

(22) Filed: Oct. 28, 1999

Related U.S. Application Data

(60) Provisional application No. 60/105,945, filed on Oct. 28, 1998.

(51) Int. Cl.[7] .................................................. A61B 5/00
(52) U.S. Cl. ......................... 600/310; 600/309; 600/476
(58) Field of Search ................................ 600/473, 476, 600/309–344, 369; 356/39–42, 300, 343, 369, 435, 445, 330–334; 250/493.1, 494.1, 495.1

(56) References Cited

U.S. PATENT DOCUMENTS

| | | | |
|---|---|---|---|
| 4,321,930 A | | 3/1982 | Jöbsis et al. |
| 4,556,057 A | | 12/1985 | Hiruma et al. |
| 4,573,761 A | | 3/1986 | McLachlan et al. |
| 5,042,494 A | | 8/1991 | Alfano |
| 5,212,537 A | | 5/1993 | Birang et al. |
| 5,241,368 A | | 8/1993 | Ponstingl et al. |
| 5,297,554 A | * | 3/1994 | Glynn et al. ................ 600/476 |
| 5,298,741 A | | 3/1994 | Walt et al. |
| 5,303,026 A | | 4/1994 | Strobl et al. |
| 5,419,323 A | | 5/1995 | Kittrell et al. |
| 5,421,337 A | | 6/1995 | Richards-Kortum et al. |
| 5,421,339 A | | 6/1995 | Ramanujam et al. |
| 5,517,987 A | * | 5/1996 | Tsuchiya .................... 600/328 |
| 5,534,997 A | | 7/1996 | Schrader |
| 5,555,885 A | * | 9/1996 | Chance ....................... 600/431 |
| 5,562,100 A | | 10/1996 | Kittrell et al. |
| 5,581,648 A | | 12/1996 | Sahagen |
| 5,612,540 A | | 3/1997 | Richards-Kortum et al. |
| 5,625,458 A | | 4/1997 | Alfano et al. |

(List continued on next page.)

OTHER PUBLICATIONS

Guillermo Marquez and Lihong V. Wong, "White light oblique incidence reflectometer fro measuring absorption and reduced scattering spectra of tissue–like turbid media," OPTICS EXPRESS, vol. 1, No. 13, pp. 454–460. (Dec. 22, 1997).*

Bigio, I. et al., "Determination of the Cervical Transformation Zone Using Elastic–Scattering Spectroscopy", *SPIE*, vol. 2679, pp. 85–91 (1996).

Ramanujam, N. et al., "Development of a Multivariate Statistical Algorithm to Analyze Human Cervical Tissue Fluorescence Spectra Acquired In Vivo", *Lasers in Surgery and Medicine*, vol. 19, pp. 46–62 (1996).

*Primary Examiner*—Eric F. Winakur
*Assistant Examiner*—Matthew Kremer
(74) *Attorney, Agent, or Firm*—Merchant & Gould P.C.

(57) ABSTRACT

A probe for the characterization of optical properties, including scattering and absorption properties of a sample, such as medical and industrial samples, includes an illumination fiber to radiate light toward an object and at least two collection fibers to receive light diffusely reflected from the object. At least two of the collection fibers are spaced at different distances from the illumination fiber. A region of the sample is illuminated with light from the illumination fiber. A portion of the light is diffusely reflected by the region. A portion of the diffusely reflected light is received by the two or more collection fibers. The region is characterized based on an amount of light received by each of the collection fibers. When the method is used for medical purposes, the characterization of the region may be used to make a diagnosis.

46 Claims, 12 Drawing Sheets

U.S. PATENT DOCUMENTS

| | | |
|---|---|---|
| 5,634,922 A | 6/1997 | Hirano et al. |
| 5,657,404 A | 8/1997 | Buchanan et al. |
| 5,676,143 A * | 10/1997 | Simonsen et al. ........... 600/316 |
| 5,687,730 A | 11/1997 | Doiron et al. |
| 5,697,373 A | 12/1997 | Richards-Kortum et al. |
| 5,699,795 A | 12/1997 | Richards-Kortum et al. |
| 5,825,488 A * | 10/1998 | Kohl et al. ................. 356/342 |
| 5,926,262 A * | 7/1999 | Jung et al. .................... 357/73 |
| 5,931,779 A * | 8/1999 | Arakaki et al. ............. 600/310 |
| 6,016,435 A * | 1/2000 | Maruo et al. ................ 600/316 |
| 6,041,247 A * | 3/2000 | Weckstrom et al. ........ 600/323 |
| 6,078,833 A * | 6/2000 | Hueber ........................ 600/476 |
| 6,124,597 A * | 9/2000 | Shehada et al. ............ 250/461 |

* cited by examiner

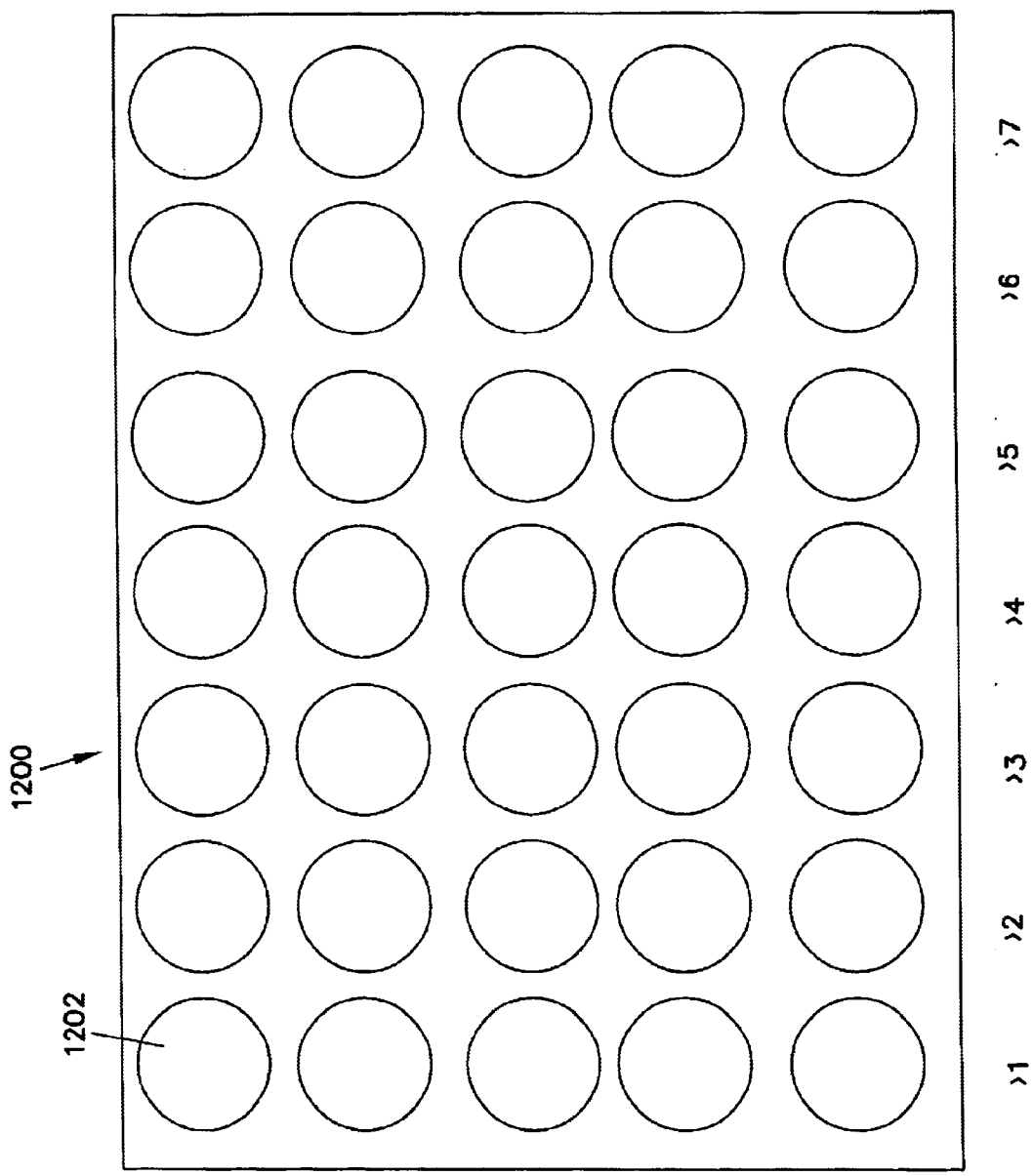

OPTICAL FIBER PROBE AND METHODS FOR MEASURING OPTICAL PROPERTIES

This application claims priority from provisional application Serial No. 60/105,945 filed Oct. 28, 1998, and which is incorporated herein by reference.

FIELD OF THE INVENTION

The present invention is directed generally to an optical fiber probe and methods measuring optical properties. In particular, the present invention is directed to an optical fiber probe and methods for observing light diffusely reflected from an object at spatially separated locations.

BACKGROUND OF THE INVENTION

Optical methods have been widely used to characterize the physical and chemical properties of materials. These methods are typically based on various modes of interaction of light with a sample. These interactions can be described as various optical properties of the sample and can often be used to identify or distinguish different materials.

Optical methods can be used in industrial environments to monitor the progress of chemical reactions and the concentration of the various components in a process stream. Additionally, optical methods can be used to determine trace impurities in chemicals. In many instances, samples must be removed from a reactor or process stream for analysis. New non-destructive and non-invasive characterization methods are needed to monitor reactions on a continuous basis.

Many conventional optical techniques are based on the absorption of light by a chemical species. The amount of light absorbed is often proportional to the concentration of the chemical present. Typically, absorption of light is determined by measuring the amount of light transmitted through a sample. A disadvantage of many techniques based on determining the absorption or transmission of light is the need for dilute samples to obtain accurate quantitative results. If the concentration is too high, scattering becomes significant and/or transmission of light through the sample is low. Consequently, industrial chemical process streams frequently are not amenable to absorption techniques because of high concentrations or turbidity.

Another optical property that can be observed is fluorescence in which a chemical species absorbs light of a particular wavelength and emits light at another wavelength. Unlike absorption techniques that generally measure the amount of transmitted light, fluorescence techniques do not require that the illumination light beam pass through the sample. This permits the application of fluorescence techniques to turbid or opaque samples.

Conventional fluorescent techniques have been used in medical diagnosis. In some instances, cells or tissue have natural chromophores so that dyes may not be needed to detect abnormal cells or tissue. However, in many cases, the tissue or cells must be brought in contact with a dye that is selectively retained by either diseased or healthy cells or tissue. The dye fluoresces when irradiated and helps locate abnormal tissue. To be effective, a dye must be found that is selectively retained by the diseased or healthy cells or tissue and is also suitable for use in humans.

Although, illumination by light at multiple wavelengths can provide a characteristic fluorescence spectrum of the tissue or cells, in many cases, the amount of fluorescent light reaching a detector is very low because of low quantum yields for fluorescence. Additionally, because fluorescent light is emitted uniformly in all directions, only a small portion of the light is typically directed toward a detector. Therefore, there is a need to provide new probes and techniques for the determination of optical properties of samples, including, for example, the diagnosis of cells or tissue and/or the characterization of components in an industrial chemical process stream.

SUMMARY OF THE INVENTION

Generally, the present invention relates to a method of determining optical properties, including scattering and/or absorption properties, to characterize samples, including medical and industrial samples, and a probe for use in the method. One embodiment is a probe including an illumination fiber to radiate light toward an object and at least two collection fibers to receive light from the object. At least two of the collection fibers are spaced at different distances from the illumination fiber.

Another embodiment of the invention is a probe assembly including a light source, an illumination fiber coupled to the light source to radiate light toward an object, two or more collection fibers to receive light from the object, and a detector for measuring a characteristic, such as the intensity, of the light from the collection fiber. At least two of the collection fibers are spaced at different distances from the illumination fiber.

Yet another embodiment is a method of characterizing a region of a sample. The region is illuminated with light from an illumination fiber. A portion of the light is diffusely reflected by the region. A portion of the diffusely reflected light is received by two or more collection fibers, at least two of which are spaced at different distances from the illumination fiber. The region is characterized based on an amount of light received by each of the collection fibers. When the method is used for medical diagnostic purposes, the characterization of the region may be used to make a diagnosis.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 12 is one example of a detector array, according to the invention for use in the probe assembly of FIG. 11.

Figure 1:
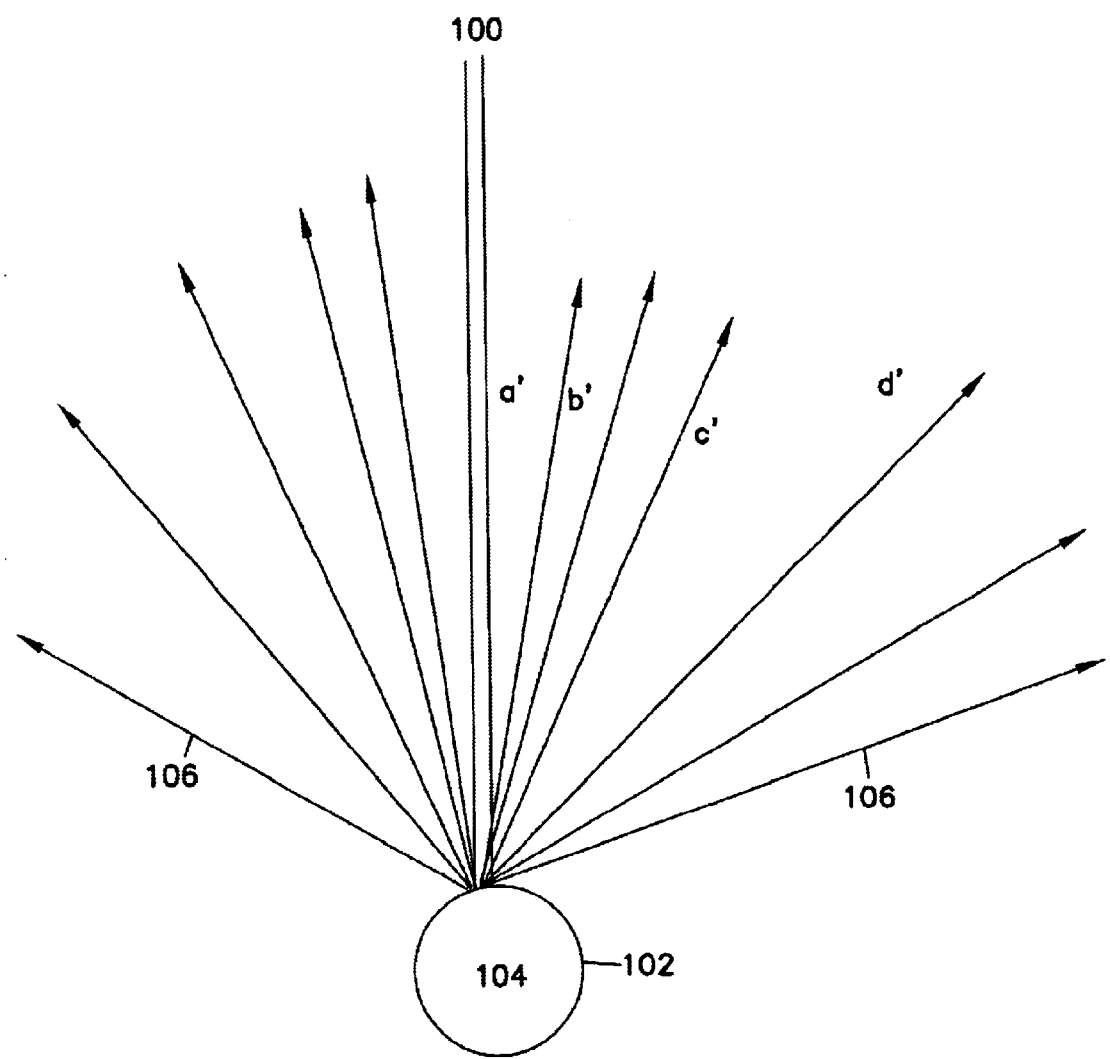
FIG. 1 is a diagrammatic representation of light scattering off a particle.

While the invention is amenable to various modifications and alternate forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The present invention is believed to be applicable to probes and techniques for determination of the optical properties of medical, industrial, and other samples. In particular, this invention is directed to a fiber optic probe and a method of using the fiber optic probe to determine optical properties such as, for example, diffuse reflectance of the sample, scattering and/or absorption coefficients, and scattering and/or absorption spectra of an object. While the present invention is not so limited, an appreciation of various aspects of the invention will be gained through a discussion of the embodiments provided below.

In industrial processes, such as, for example, food processing or pharmaceutical manufacturing, two materials can be visually indistinguishable, but perform very differently. Likewise, in medical applications, diseased tissue may appear very similar to normal tissue. Optical properties are often useful to characterize such samples. A variety of optical properties may be used including, for example, absorption, transmission, scattering, fluorescence, and others. One or more of these characterization methods can be used to differentiate between samples. The determination of the diffuse reflectance of a sample illuminated by a light source can be useful because diffuse reflectance is dependent on factors such as, for example, scattering and absorption of light by the sample.

An advantage of optical methods based on diffuse reflectance of a sample is that thick, non-transparent samples can be studied. Thus, such methods are often applicable in industrial environments where the samples are opaque or turbid and in a medical environment to diagnose tissue abnormalities or diseases. The amount of light diffusely reflected by a sample is typically dependent on the composition of the industrial sample or human tissue allowing for differentiation. For example, healthy tissue may have scattering and absorption characteristics different from those of diseased or abnormal tissue.

Figure 2:
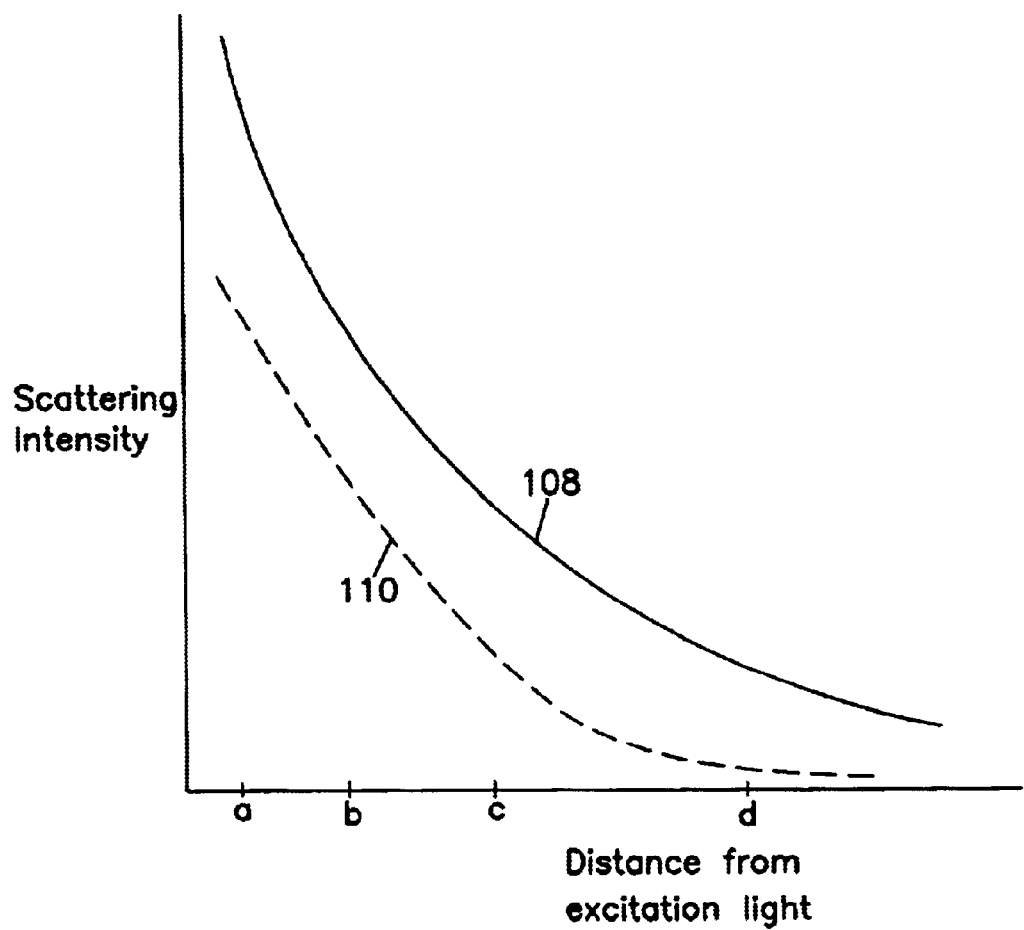
FIG. 2 is a graph of intensity versus lateral distance from an illumination source for light scattered by a particle.

The diffuse reflectance characteristics of a sample typically depend, at least in part, on the scattering characteristics of the sample. When light strikes a sample, a portion of the light collides with and scatters from particles in the sample, as illustrated in FIG. 1. An illumination light beam 100 strikes the surface 102 of a particle 104 and light 106 is scattered in many directions. An exemplary plot 108 of scattering intensity as a function of the lateral distance from the illumination light beam, as shown in FIG. 2, illustrates that the scattered light intensity typically decreases with distance from the illumination light beam. Often with single scattering events, the scattered light intensity decreases exponentially from the illumination light beam.

In many samples, at least a portion of the light scattered from one particle collides with one or more additional particles before leaving the sample and reaching a detector. These multi-scattering events typically alter the light intensity distribution. The net result is often a diffusion of the scattering light over a greater distance from the illumination light beam.

In addition to scattering, some of the light 100 can be adsorbed by the particle 104. Consequently, the scattering light intensity is typically less if absorption occurs when the illumination light beam 100 strikes the particle 104. This is illustrated by the dashed curve 110 in FIG. 2. In addition, light scattered by one particle may be absorbed by other particles in the path of the scattered light.

Other phenomena may contribute (in many cases, in small amounts) to the intensity of light reaching a detector. For example, some of the absorbed radiation can be emitted at the same or different wavelength than the wavelength of the illumination light beam. This may occur due to fluorescence, Raleigh scattering, or Raman scattering. When multi-wavelength diffuse reflectivity spectra are obtained, the intensity of light received at a detector at a particular wavelength may be enhanced due to these phenomena.

All of these phenomena contribute to the intensity of light (e.g., diffusely reflected light) collected by a detector. When the intensity of this light is recorded as a function of wavelength, the spectrum may be affected by the amount of light the sample absorbs or emits in that wavelength region. The light intensity may be diminished in areas where the sample absorbs and may be increased in wavelength regions that the sample emits when excited. Consequently, the diffuse reflectivity spectrum reveals information about the scattering, absorption, fluorescence, and/or other optical characteristics of a sample.

In contrast to conventional measurements that in many instances only use one detector, the intensity of diffusely reflected light is determined at two or more distances from the illumination light beam. In this manner, an intensity distribution, such as that shown in FIG. 2, can be obtained. This intensity distribution can then be used to distinguish samples of different tissues for medical purposes or different compositions for industrial purposes by, for example, comparison of the measured light intensity distributions and/or numerical characteristics derived from the light intensity distributions. This can be accomplished by, for example, illuminating the sample with a light beam and measuring the diffuse reflectivity of the sample at two or more locations that are spaced at different distances from the light beam. In one embodiment, optical fibers are used to provide the light beam and to collect the diffusely reflected light. Optical fibers are particularly useful because of their compactness and good light transport characteristics.

Figure 3:
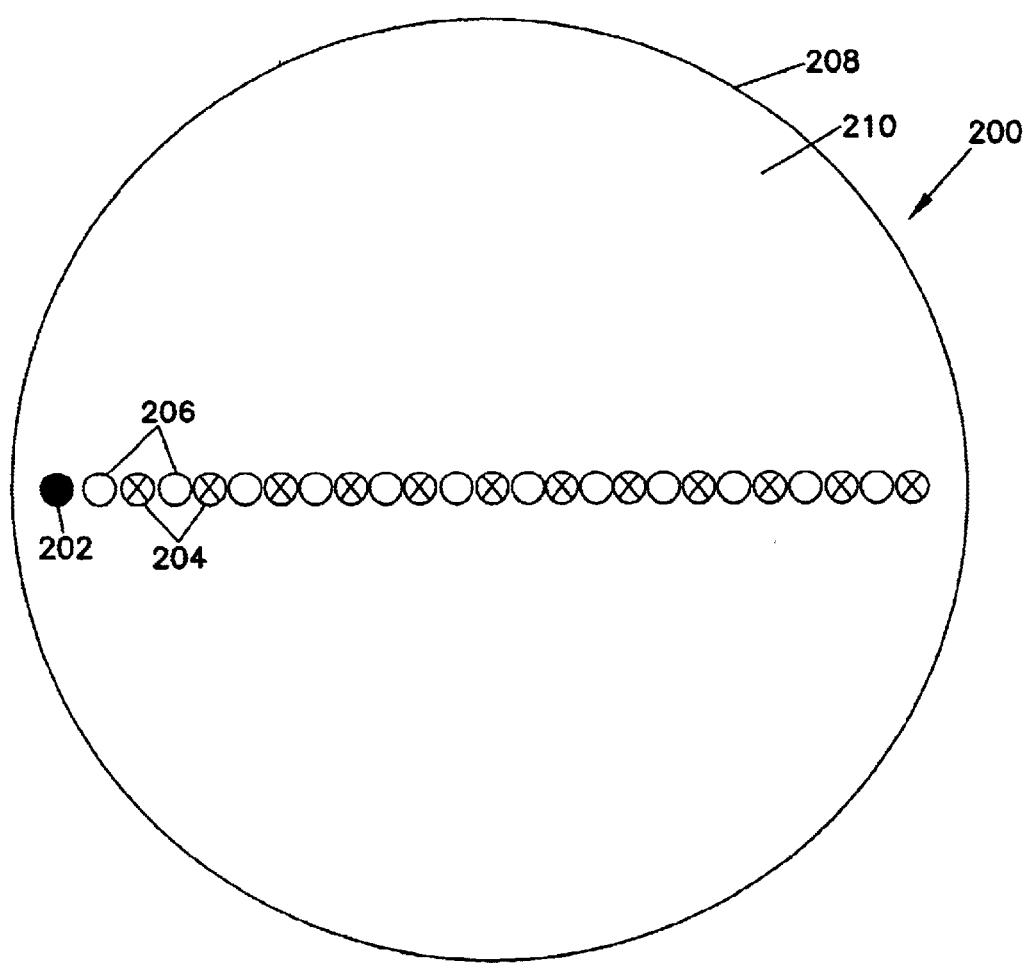
FIG. 3 is a first embodiment of an optical fiber probe according to the invention.

FIG. 3 illustrates a fiber optic probe 200 in accordance with an embodiment of the invention. The probe includes an illumination fiber 202 for radiating light toward an object and two or more collection fibers 204 spatially separated from the illumination fiber 202 for receiving light emerging from the object. In the illustrated embodiment, the illumination fiber 202 and the collection fibers 204 are arranged in a linear fashion with the illumination fiber 202 at one end of the linear arrangement. In this particular embodiment, each of the collection fibers 204 is at a different distance from the illumination fiber 202. In some embodiments, however, more than one collection fiber 204 may be at the same distance from the illumination fiber 202.

One or more of the collection fibers 202 may be immediately adjacent to the illumination fiber or separated from the illumination fiber 202 by a spacer 206. In the embodiment illustrated in FIG. 3, there is a spacer 206 between the illumination fiber 202 and the nearest collection fiber. Likewise, the collection fibers 204 may be immediately adjacent to each other or separated by spacers 206. FIG. 3 illustrates an embodiment with a spacer 206 between each pair of collection fibers 204. Another embodiment of a fiber optic probe 300, shown in FIG. 4, includes a linear array of optical fibers with an illumination fiber 302 at one end and collection fibers 304 extending along the linear array without any intervening spacers.

Figure 4:
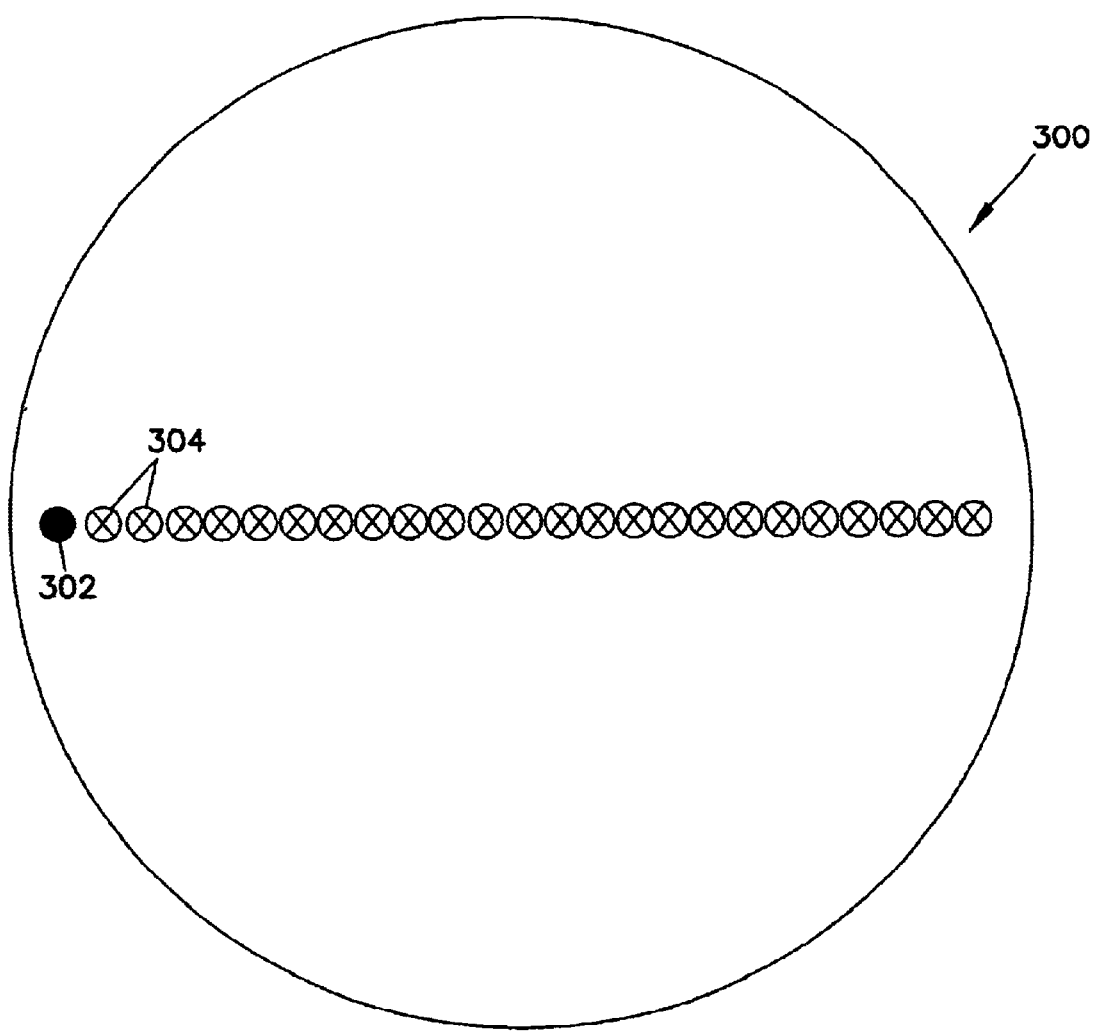
FIG. 4 is a second embodiment of an optical fiber probe according to the invention.

Although the fiber optic probe may be formed without spacers, as shown in FIG. 4, spacers may be advantageous. Optical fibers typically receive light from a cone shaped volume extending from the tip of the fiber into the sample. Because the shape is conical rather than cylindrical, spacers may reduce the volume of sample that two adjacent fibers are simultaneously sampling. The cone shaped sampling volume is typically attributable to the construction of the optical fibers.

Figure 5:
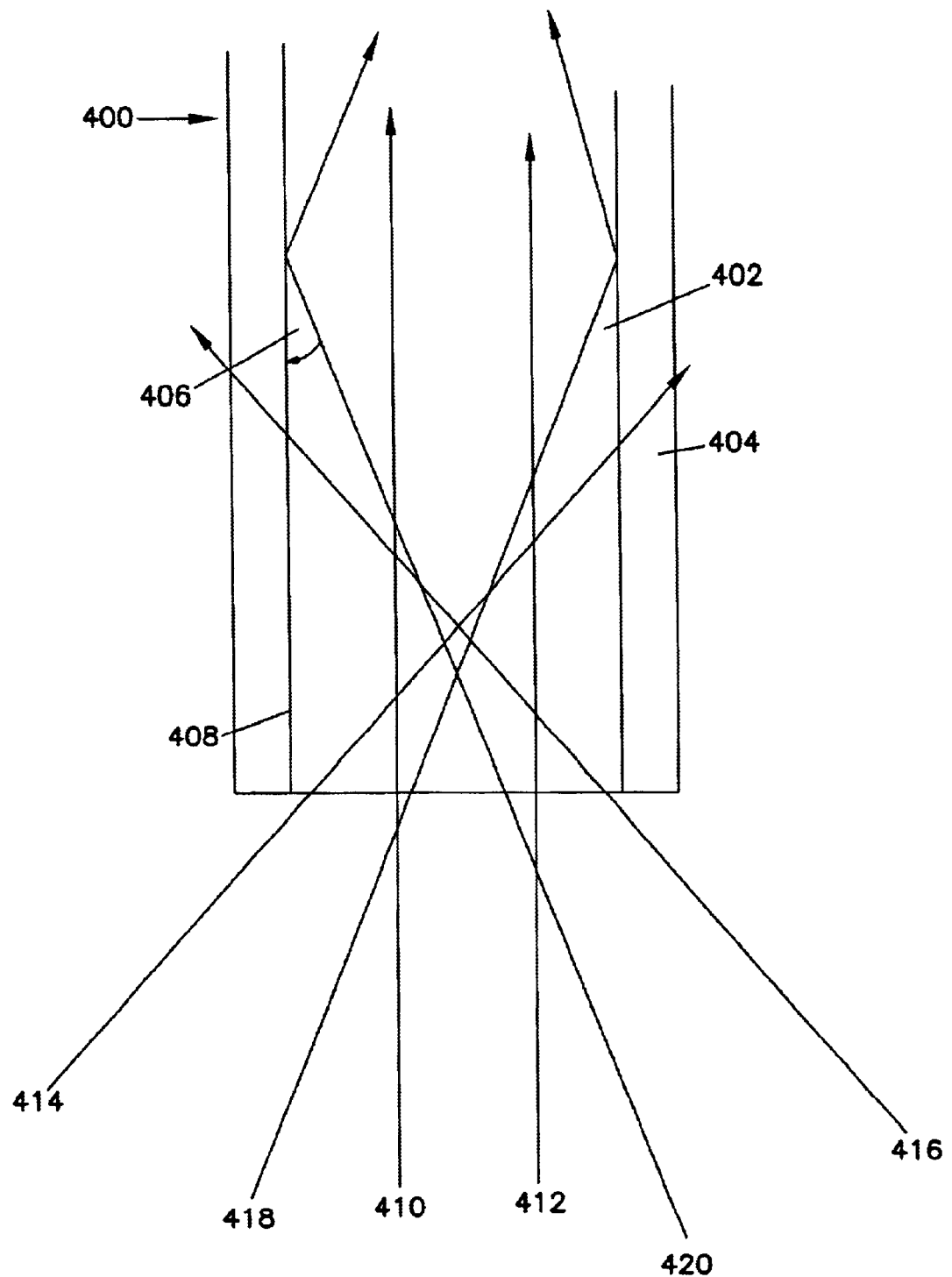
FIG. 5 is a diagrammatic representation of light interacting with an optical fiber.

Optical fibers 400 are often made of a core material 402 surrounded by a cladding material 404, as shown in FIG. 5. The cladding material 404 typically has a lower index of refraction than the core material 402. In order for light to be totally reflected at the interface between the core 402 and the cladding 404, the angle 406 formed between the light ray and the surface 408 of the cladding must be less than or equal to the critical angle, $\theta_c$, as defined by the following equation:

$$\cos(\theta_c) = n_2/n_1.$$

where $n_1$ is the index of refraction of the core material 402 and $n_2$ is the index of refraction of the cladding material 404. The sum of all angles less than or equal to the critical angle defines a cone shaped volume where light can enter and be reflected from the cladding material 404 and travel down the core material 402 of the fiber optic 400. For example, light rays 410 and 412 are parallel with the cladding material 404 and travel directly through the core material 402. Light rays 414 and 416 intersect with the cladding at angles greater than the critical angle and are not reflected or only partially reflected back into the core material 402. Light from these light rays is greatly attenuated when the light exits an opposing end of the optical fiber 400. The only light that travels through the optical fiber are rays that do not intersect the cladding material 404 (rays 410 and 412) or intersect at an angle less than or equal to the critical angle (rays 418 and 420).

The preferred distance between the centers of optical fibers typically ranges from about one to about four times the diameter of the optical fibers. The diameter of the spacer is typically between 0.25 to 4 times that of the optical fibers. Spacers may be between some or all of the collection fibers and in some embodiments more than one spacer may be placed between any two optical fibers. For ease of probe fabrication, the spacers may be optical fibers that are not used for either illumination or collection purposes. However, other spacer materials can also be used. Moreover, this invention is not limited by the use of spacers to compensate or reduce the overlap in the volume sampled by adjacent collector fibers. For example, a mathematical model may be used to account for overlapping sampling volumes.

Figure 6:
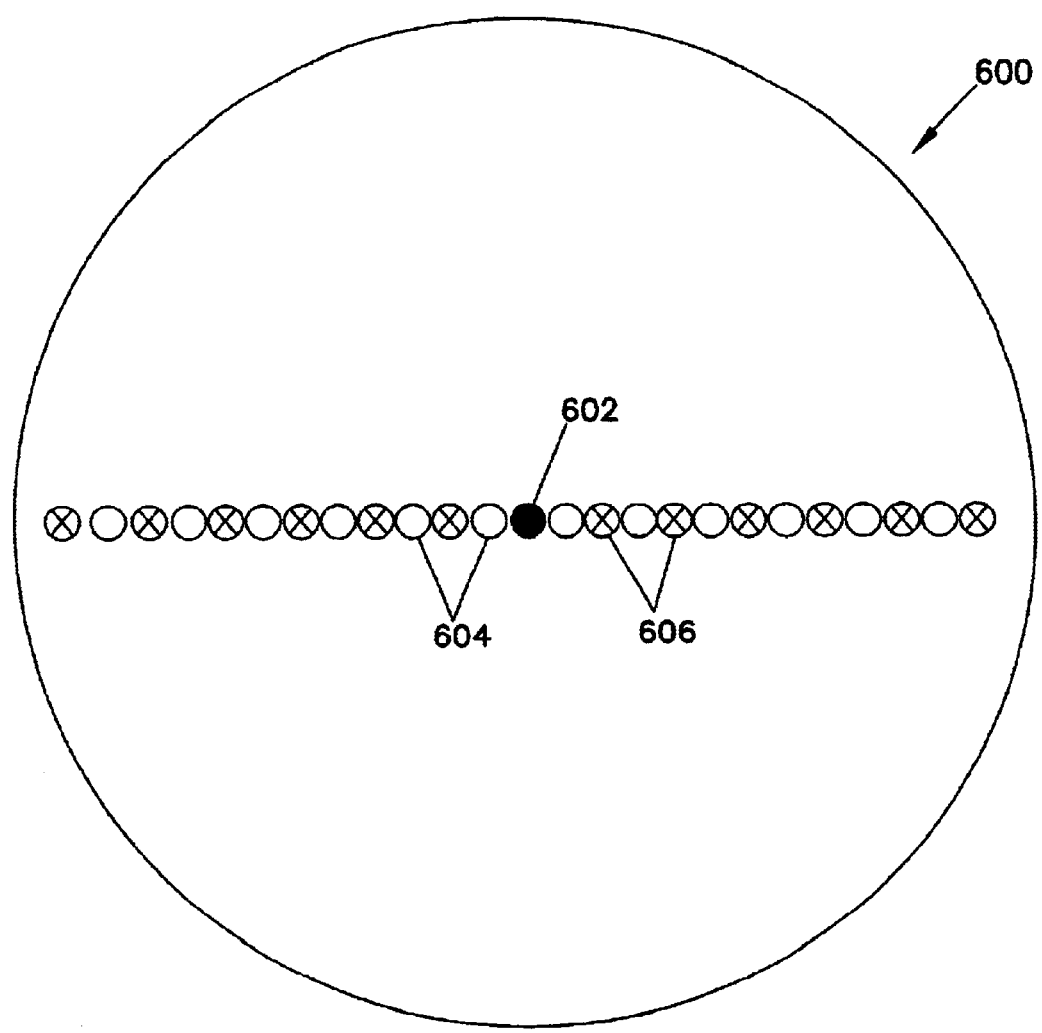
FIG. 6 is a third embodiment of an optical fiber probe according to the invention.

Other embodiments of the invention have different arrangements of optical fibers. One embodiment of an optical probe 600, illustrated in FIG. 6, has a linear arrangement of optical fibers with an illumination fiber 602 positioned within the array with collection fibers 606 extending to either side of the illumination fiber 602. This embodiment may or may not contain spacers 604. One possible position for the illumination fiber 602 is in the center of the linear array of optical fibers although this positioning is not necessary. The signals from collection fibers 606 that are spaced the same distance, but on opposite sides of the illumination fiber, can be combined, particularly, if the diffuse reflection of the illumination light by the sample is radially independent.

Figure 7:
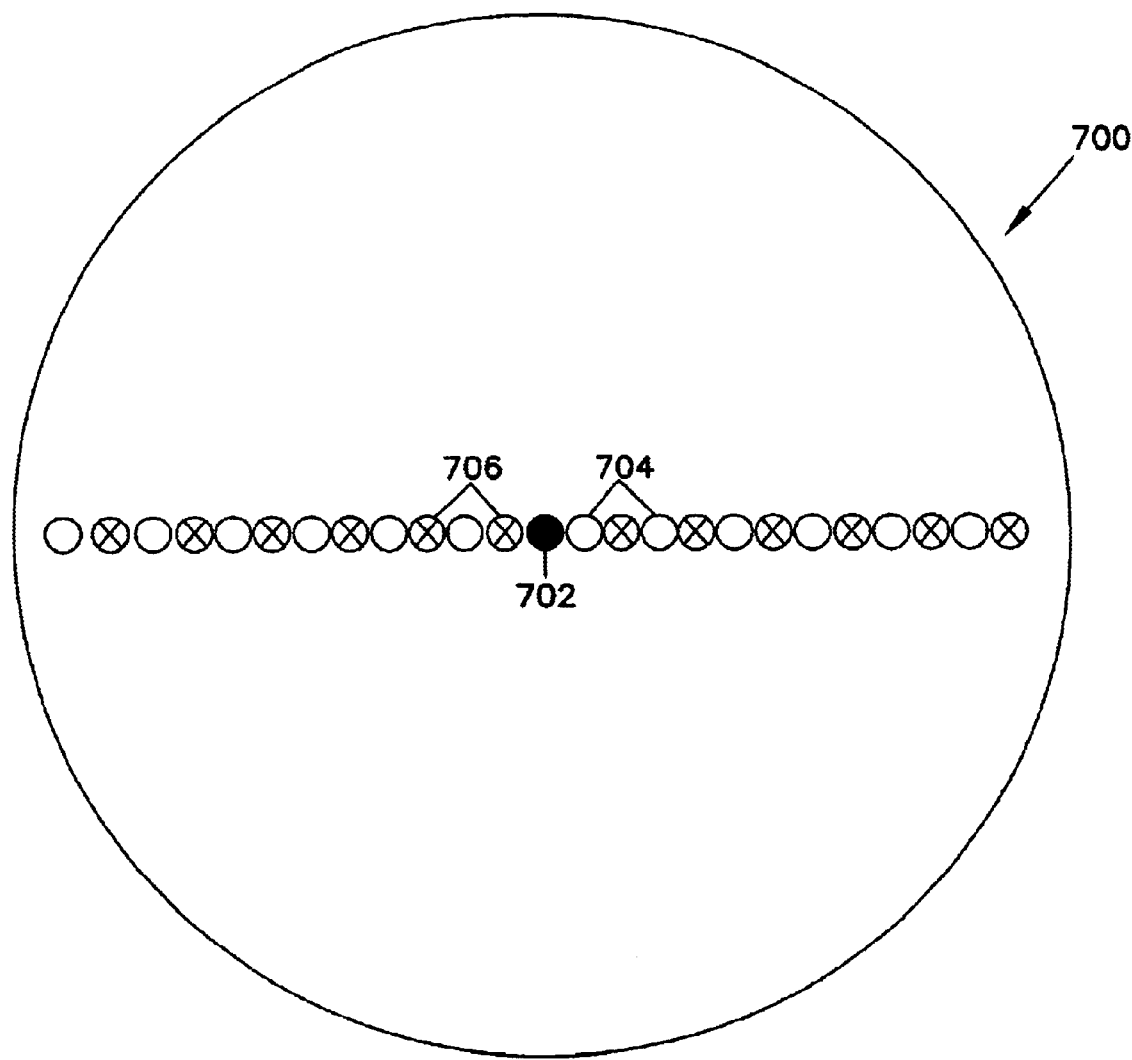
FIG. 7 is a fourth embodiment of an optical fiber probe according to the invention.

Another embodiment of an optical probe 700, illustrated in FIG. 7, includes an illumination fiber 702 with collection fibers 706 extending to either side of the illumination fiber 702. In this embodiment, the collection fibers 706 on opposite ends of the linear ray are staggered so that, for example, the nearest and third nearest collection fibers are on one side of the illumination fiber 702 while the second and fourth nearest collection fibers are on an opposite side of the illumination fiber 702. Spacers 704 are typically used in this embodiment to separate the collection fibers 706.

Figure 8:
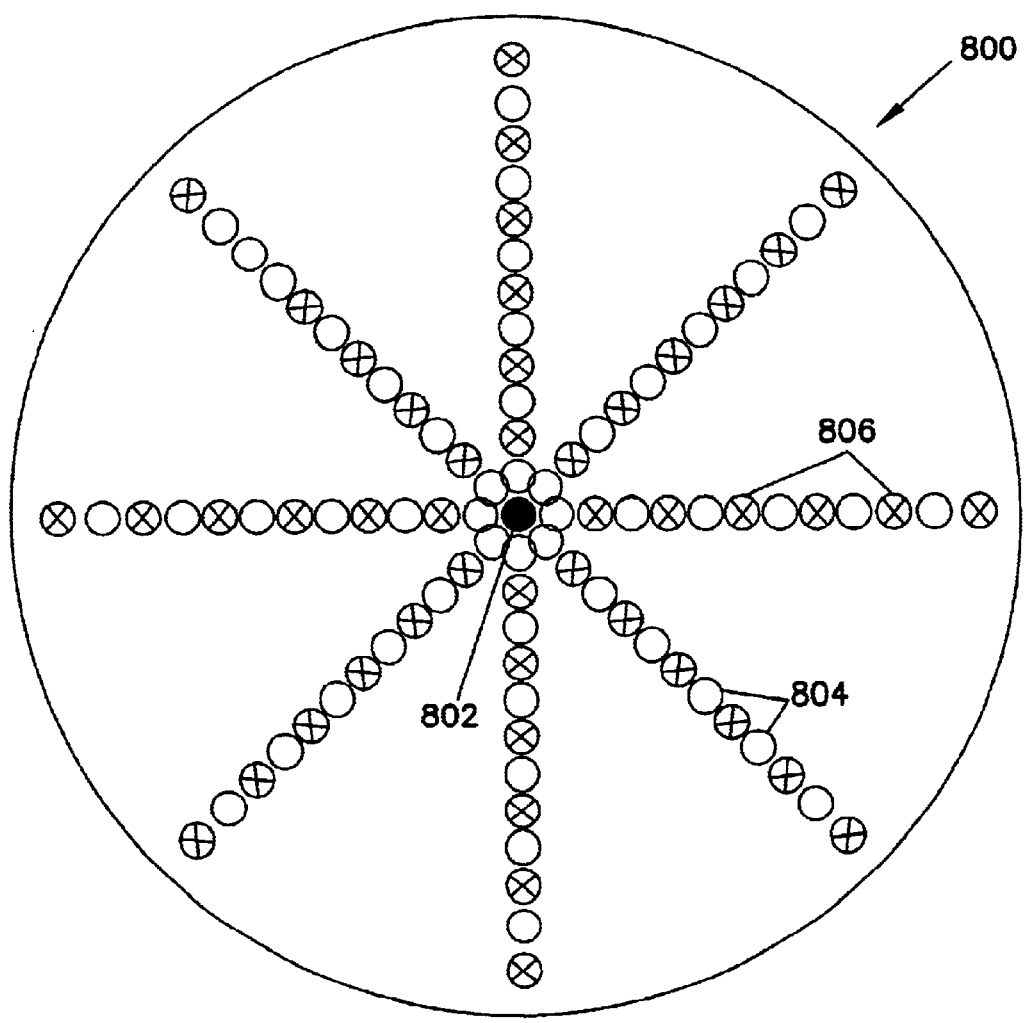
FIG. 8 is a fifth embodiment of an optical fiber probe according to the invention.

Yet another embodiment of an optical fiber probe 800 is illustrated in FIG. 8. In this embodiment an illumination fiber 802 is formed with two or more linear arrays of collection fibers 806, with or without spacers 804, extending radially from the illumination fiber 802. Again, those collection fibers 806 that are the same distance from the illumination fiber 802 can have their signals combined, particularly if the diffuse reflection of the illumination light by the sample is radially independent. This may result in an increase in signal amplitude with an improved signal-to-noise ratio as more collection fibers are used for each particular distance from the illumination fibers.

Figure 9:
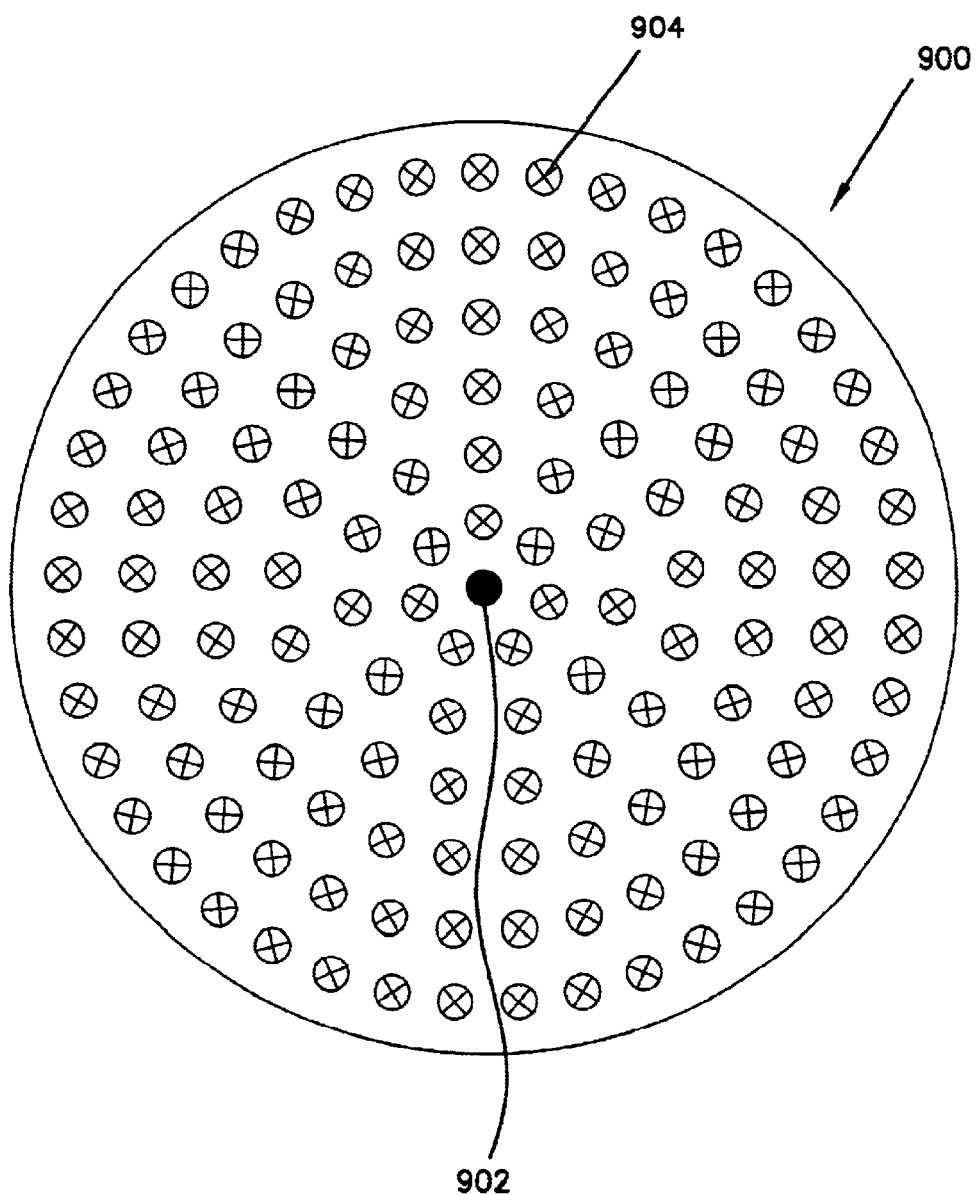
FIG. 9 is a sixth embodiment of an optical fiber probe according to the invention.

Yet another optical fiber probe 900 is illustrated in FIG. 9. In this optical fiber probe 900, an illumination fiber 902 is surrounded by concentric circles of collection fibers 904. Typically, the signals for each collection fiber 904 in a particular concentric circle can be added thereby increasing the signal-to-noise ratio particularly for those concentric circles of collection fibers 904 that are further away from the illumination fiber 902. However, it should be recognized that the signal for each concentric circle should typically be normalized for the number of collection fibers 904, and/or the combined fiber optic surface area, in each concentric circle.

Figure 10:
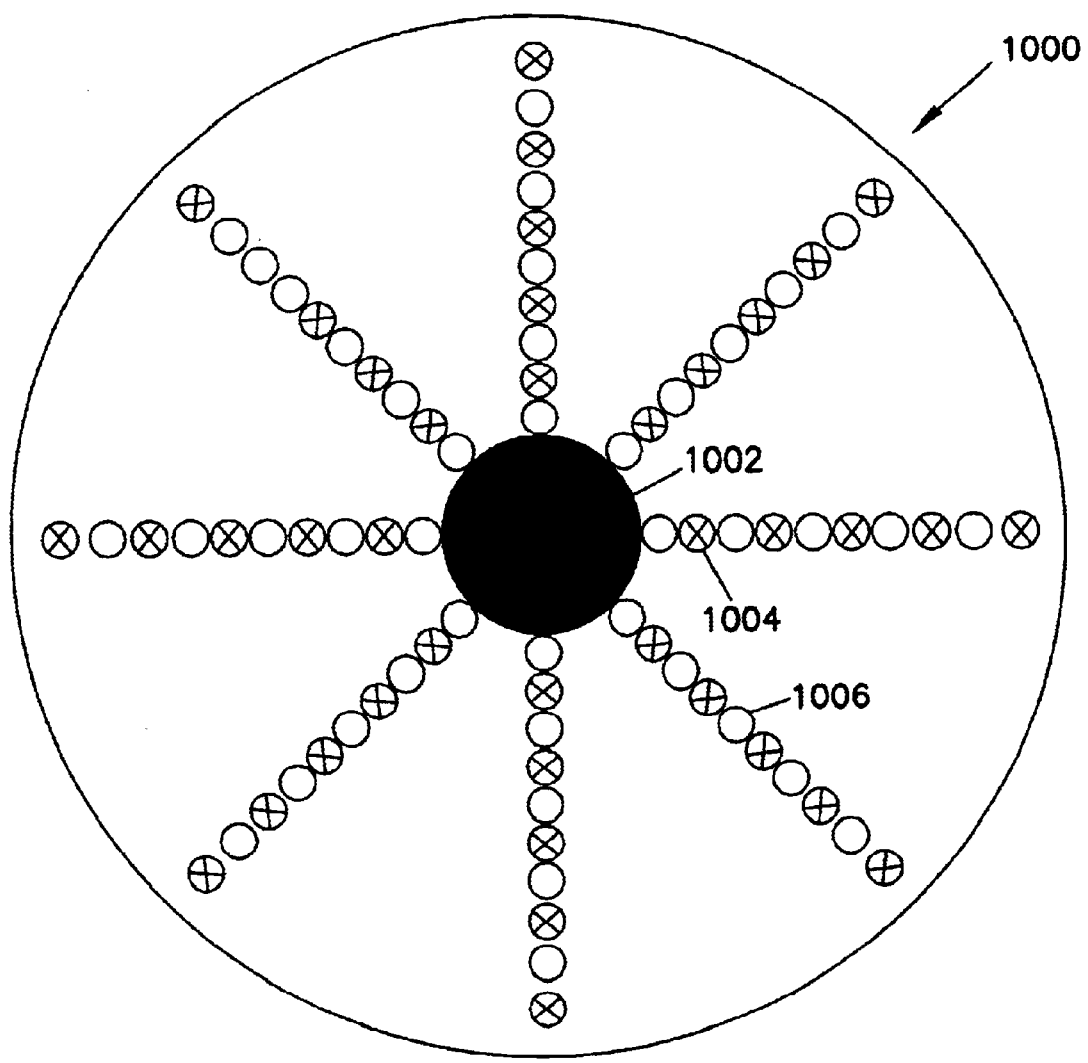
FIG. 10 is a seventh embodiment of an optical fiber probe according to the invention.

As illustrated in FIG. 10 with fiber optic probe 1000, the size of the illumination fiber 1002 can be larger (or smaller) than the size of the collection fibers 1004. A larger illumination fiber 1002 may be advantageous because more light can be directed toward the sample and the signal intensity measured at greater scattering distances may increase. A smaller illumination fiber may provide better spatial resolution of a sample as a smaller fiber typically illuminates a smaller region of the sample.

The total number of collection fibers used in any of these embodiments can vary. The number of collection fibers may be limited by considerations such as the cost of the probe, the size of the probe, and the sophistication of the detection system. The intensity of diffusely reflected light typically diminishes with distance of the collection fibers from the illumination fiber. The maximum distance that diffusely reflected light can be detected may be limited by the density of the scattering bodies in the sample and the sensitivity of the detection system. In some instances, the collection fibers extend from about 3 to 8 mm from the illumination fiber. However, shorter or larger arrays can also be used.

The diameter of the core of the collection fibers can range from, for example, about 50 $\mu$m to about 400 $\mu$m. Often more spatial information can be obtained using a larger number of small diameter collection fibers. However, with larger fibers, more light is collected and less sensitive detectors or shorter sampling times may be needed.

The fibers are typically prepared with quartz (particularly if ultraviolet wavelengths are to be observed) or silica cores. Other suitable materials can be used, including polymeric materials, depending, for example, on the wavelengths to be observed. One example of a suitable optical fiber is a 200 μm diameter quartz fiber (240 μm diameter with cladding) with a numerical aperture of 0.22 available from, for example, Rare Earth Medical (West Yarmouth, Mass.).

The fibers 202, 204, and 206 are encased in a housing 208 (see FIG. 3) for proper alignment of the fibers relative to each other. The housing 208 may enhance the durability of the probe. The housing is typically formed using a metal, such as, for example, a stainless steel ferule, or plastic.

The fibers can be secured within the housing 208 with a binder material 210 such as, for example, epoxy and carbon particles. Preferably, the binder material is non-fluorescent and non-reflective. For example, carbon particles in an epoxy binder material make the resulting binder opaque and optically isolates the closely-spaced optical fibers.

In many instances, a probe may be used multiple times for analysis. If used for medical applications, the probe may need to be disinfected before each use. The preferred housing and securing materials do not degrade upon disinfecting in, for example, metricide, 1% sodium hyperchlorite, or glutaraldehyde-based agents, such as Cidex® (Johnson and Johnson).

Figure 11:
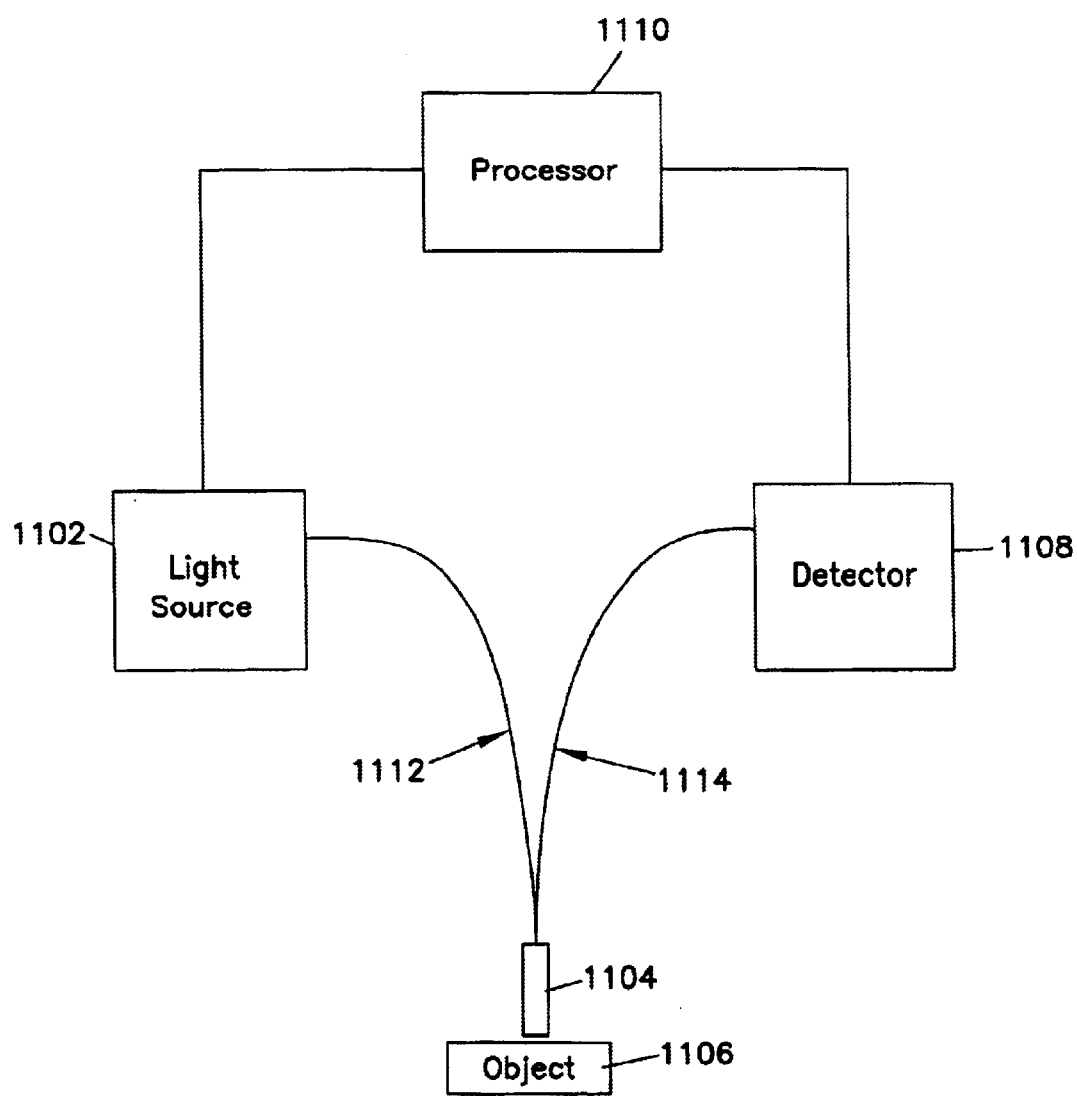
FIG. 11 is one example of a probe assembly, according to the invention, for use with any of the optical fiber probes of FIGS. 3, 4, and 6–10.

FIG. 11 illustrates a fiber optic probe assembly 1100 in accordance with an embodiment of the invention. The probe assembly comprises a light source 1102, an optical fiber probe 1104, and a detector 1108. A processor can be added to control the optical probe assembly and/or to facilitate data collection and manipulation. The optical fiber probe 1104 includes an illumination fiber or fibers 1112 coupled to the light source 1102 for irradiating an object 1106 and two or more collection fibers 1114 for receiving light diffusely reflected by the object 1106.

The light source 1102 can be, for example a laser or a lamp, such as, for example, a xenon lamp. The light can be either monochromatic or polychromatic but a polychromatic source may be advantageous when diffuse reflectance over a range of wavelengths is measured. A xenon lamp is an example of a preferred light source because it can provide light over a wavelength region of 200 nm to 800 nm. The light source 1102 can illuminate the sample with wavelengths of light in the visible and near ultraviolet regions of the electromagnetic spectrum. Infrared light may be removed in some instances, using, for example, a filter, because infrared light may heat the sample and/or degrade the probe. The light source 1102 can be constant or pulsed. A shutter (not shown) can also be included between the light source 1102 and the object 1106 to control the amount of time the object 1106 is exposed to light.

One embodiment of a suitable detector 1108 includes a spectrograph and a detector array such as, for example, a CCD (charge-coupled device) array or a photodiode and/or photomultiplier array. The spectrograph disperses the incoming light using, for example, a prism or diffraction grating. The detector array measures the amount of light from the collection fibers.

As illustrated in FIG. 12, the detector array 1200 is an array of individual detector units 1202, such as CCD or photodiode and/or photomultiplier units, that can measure the intensity of light received by each of the collection fibers. For example, one or more rows of the detector array may correspond to an individual collection fiber. In one embodiment, individual detector units have a diameter that is less than the diameter of the collection fiber (e.g., 15 to 25 μm diameter detector units in use with a 200 μm diameter collection fiber), so that more than one row of detector units corresponds to each optical fiber. The spectrograph disperses the light to form individual wavelength regions that are measured along the columns of the detector array. This permits the simultaneous measurement of a spectrum for each collection fiber as a function of wavelength.

The number of collection fibers and the number of wavelength regions that can be monitored often correspond with the size of the detector array. The detector array can have any size One suitable detector array includes 512 by 512 individual detector units, although larger (e.g., 1024 by 1024 arrays) or smaller arrays can be used. Data read-out and computational times are typically dependent on the size of the array.

This particular detector provides spatial information about the diffuse reflectance of the sample at a number of illumination wavelengths. An entire spectrum ranging from, for example, 200 to 800 nm can be observed simultaneously for each collection fiber. Narrower and broader ranges can also be observed by adjusting, for example, the extent of dispersion by the spectrograph and the size of the detector array.

A simpler detection system can also be used, particularly, for example, if monochromatic light from a laser is used to irradiate the sample. In this case, the detector only observes light at a single wavelength. A simple photodiode and/or photomultiplier tube, for example, can be used to measure the light intensity at each collection fiber. Even with this simple detection system, data at various wavelengths can be obtained by tuning the laser or using different lasers for different illumination wavelengths.

A processor 1110 may be added to the probe assembly to facilitate data handling and calculation of parameters or characteristics based on the intensity of light received at each collection fiber and/or at multiple illumination wavelengths. For example, the processor 1110 can characterize the light intensity as a function of distance from the illumination light beam, plot the light intensity as a function of wavelength to obtain a spectrum, and calculate, for example, scattering and/or absorption coefficients or other optical characteristics for the sample. Additionally, the processor may be used to compare scattering and/or absorption coefficients or spectra of samples to those of previously characterized reference materials.

Collection of diffusely reflected light intensity at two or more distances from the illumination fiber provides information about the density of scattering bodies within a sample. Coupled with a polychromatic light source for illumination of the sample, diffuse reflectance data at multiple wavelengths and distances from the illumination light beam can be acquired. A diffuse reflectance spectrum can be obtained for wavelengths of light, for example, in the visible and near ultraviolet regions. In conjunction with appropriate mathematical models of light transport, optical properties of the sample can be deduced, calculated, or otherwise determined. These optical properties can yield information about the chemistry of the sample or the optical properties can be compared to those previously obtained from other samples or from other regions of the same sample.

If the constituents or regions of the sample are different, the scattering and/or absorption coefficients and spectra are often different. Therefore, scattering or absorption (as determined from the spectra) can be used to differentiate, for example, tissue types or various industrial compositions. These techniques may be used to differentiate between healthy and abnormal tissue to help find diseased tissue or to differentiate between industrial samples that are, for example, visually similar.

For samples and/or at wavelengths (such as the near infrared for many biological samples) where absorption is negligible, the propagation of light (i.e., photons) through the sample can be approximately modeled by diffusion equations. The best fit of the model to the measured data can be obtained to determine optical properties, such as, for example, a scattering coefficient.

For many biological samples, however, this approximation is not valid in the visible or near ultraviolet regions, as absorption by chromophores like hemoglobin and proteins can be significant. Alternative models, incorporating, for example, diffusion and absorption characteristics, may be used to more accurately model the optical properties of these samples and to then obtain optical characteristics based upon the measurements of spatially-resolved diffuse reflectance.

One such method that can be used to model the complex optical interactions is based on Monte Carlo calculations. In this method, a Monte Carlo-based model could be used to simulate the diffuse reflectivity monitored by the fiber array. For example, the model can be run for numerous combinations of characteristics (e.g., scattering and/or absorption coefficients) and the results can be assembled into a look-up table. Diffuse reflectivity measurements from "unknown" samples could then be compared with the data in the look-up table to determine the optical characteristics (e.g., scattering and/or absorption coefficients) for the "unknown" sample.

In some instances, for example, for medical diagnosis, tables of scattering coefficients and/or scattering spectra can be compiled for an assortment of healthy and diseased tissues as references for tissues under investigation. This method can be used to perform a non-invasive "optical biopsy" where the sample is compared to a collection of spectral signatures at a variety of source detector separations for a variety of tissues that are correlated to traditional pathology markers. Such real time medical diagnosis has the potential to expedite the therapeutic process.

It may be useful to obtain optical characteristics at a number of positions in a sample (e.g., a tissue sample). In some embodiments, the probe can be slowly moved over the surface of a sample collecting data at various points on the sample. By moving the probe incrementally in horizontal and/or lateral directions the optical characteristics of a larger region of a sample can be determined. The movement may be controlled, for example, by the processor or a separate control unit. An image of the sample can be created based on the data. For example, the image can be created by plotting the scattering or absorption coefficient at a particular wavelength for each position of the probe. The image created can then be compared to those of previously characterized materials.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

We claim:

1. A probe assembly comprising:
   a probe comprising:
      an illumination fiber to radiate light in a wavelength range of about 200 to about 800 nm toward an object;
      a plurality of collection fibers spatially separated from the illumination fiber to receive light from the object; and
      at least one spacer;
      wherein at least two of the collection fibers are at different distances from the illumination fiber, wherein each individual collection fiber is spatially separated from every other collection fiber by at least one of said spacers, wherein said probe is utilized to calculate at least a scattering coefficient of said light from said object, and wherein said scattering coefficient is utilized to characterize a region of said object,
      wherein the illumination fiber and the collection fibers form a linear arrangement and the illumination fiber is located at one end of the linear arrangement;
   a light source; and
   a detector for calculating at least a scattering coefficient of the light received by the collection fibers, wherein said scattering coefficient is utilized to characterize a region of said object.

2. The probe assembly of claim 1, wherein the detector is configured and arranged to measure an intensity of the light received by the collection fibers.

3. The probe assembly of claim 1, further comprising a processor to analyze the light received by the collection fibers.

4. The probe assembly of claim 3, wherein the processor is configured and arranged to calculate a scattering coefficient from the light received by the collection fibers.

5. The probe assembly of claim 1, wherein the light source produces two or more wavelengths of light.

6. The probe assembly of claim 1, wherein the light source comprises a laser or a lamp.

7. The probe assembly of claim 1, wherein a detector is configured and arranged to detect light in a wavelength range of from about 200 to 800 nm.

8. The probe assembly of claim 1, wherein the detector comprises a detector array and a spectrograph.

9. The probe assembly of claim 8, wherein the detector array comprises an array of charge-coupled devices.

10. The probe assembly of claim 1, wherein the illumination fiber and the collection fibers are fabricated within a non-fluorescent housing.

11. The probe assembly of claim 1, wherein the collection fibers are located at regular intervals from the illumination fiber.

12. The probe assembly of claim 1, wherein said at least one spacer comprises a fiber.

13. The probe assembly of claim 1, further comprising a spacer between the illumination fiber and a nearest collection fiber.

14. The probe assembly of claim 1, further comprising a spacer between each of the collection fibers.

15. The probe assembly of claim 1, wherein the number of collection fibers ranges from 5 to 15.

16. The probe assembly of claim 1, wherein the collection fibers extend about 3 to 8 mm from the illumination fiber.

17. The probe assembly of claim 1, wherein the diameter of the collection fibers ranges from about 50 $\mu$m to about 400 $\mu$m.

18. A probe assembly comprising:
   a probe comprising:
      an illumination fiber to radiate light in a wavelength range of about 200 to about 800 nm toward an object;
      a plurality of collection fibers spatially separated from the illumination fiber to receive light from the object; and
      at least one spacer;
      wherein at least two of the collection fibers are at different distances from the illumination fiber, wherein each individual collection fiber is spatially separated from every other collection fiber by at least one of said spacers, wherein said probe is utilized to calculate at least a scattering coefficient of said light from said object, and wherein said scattering coefficient is utilized to characterize a region of said object, wherein the collection fibers are arranged in a plurality of concentric circles about the illumination fiber;

a light source; and a detector for calculating at least a scattering coefficient of the light received by the collection fibers, wherein said scattering coefficient is utilized to characterize a region of said object.

19. The probe assembly of claim 18, wherein the detector is configured and arranged to measure an intensity of the light received by the collection fibers.

20. The probe assembly of claim 18, further comprising a processor to analyze the light received by the collection fibers.

21. The probe assembly of claim 20, wherein the processor is configured and arranged to calculate a scattering coefficient from the light received by the collection fibers.

22. The probe assembly of claim 18, wherein the light source produces two or more wavelengths of light.

23. The probe assembly of claim 18, wherein the light source comprises a laser or a lamp.

24. The probe assembly of claim 18, wherein a detector is configured and arranged to detect light in a wavelength range of from about 200 to 800 nm.

25. The probe assembly of claim 18, wherein the detector comprises a detector array and a spectrograph.

26. The probe assembly of claim 25, wherein the detector array comprises an array of charge-coupled devices.

27. The probe assembly of claim 18, wherein the illumination fiber and the collection fibers are fabricated within a non-fluorescent housing.

28. The probe assembly of claim 18, wherein the collection fibers are located at regular intervals from the illumination fiber.

29. The probe assembly of claim 18, wherein said at least one spacer comprises a fiber.

30. The probe assembly of claim 18, further comprising a spacer between the illumination fiber and a nearest collection fiber.

31. The probe assembly of claim 18, further comprising a spacer between each of the collection fibers.

32. The probe assembly of claim 18, wherein the number of collection fibers ranges from 5 to 15.

33. The probe assembly of claim 18, wherein the collection fibers extend about 3 to 8 mm from the illumination fiber.

34. The probe assembly of claim 18, wherein more than one collection fiber is at a same distance from the illumination fiber.

35. The probe assembly of claim 18, wherein the diameter of the collection fibers ranges from about 50 $\mu$m to about 400 $\mu$m.

36. A method for characterizing a region of a sample comprising:

illuminating a region of a sample with light in a wavelength range of about 200 to about 800 nm from an illumination fiber;

diffusely reflecting a portion of the light that illuminates the region;

receiving a portion of the diffusely reflected light at a plurality of collection fibers, wherein at least two of the collection fibers are at different distances from the illumination fiber, and wherein the collection fibers are spatially separated by spacers;

combining the portion of diffusely reflected light collected at two or more collection fibers; and characterizing the region based on at least a calculated scattering coefficient of the diffusely reflected light received by each of the collection fibers.

37. The method of claim 36, wherein the illumination fiber and the collection fibers form a linear arrangement.

38. The method of claim 36, wherein the two or more collection fibers from which the amount of light is combined are at a same radial distance from the illumination fiber.

39. The method of claim 36, further comprising determining the scattering coefficient from an amount of diffusely reflective light received by each of the collection fibers.

40. The method of claim 36, further comprising moving the illumination and collection fibers along the surface of the sample to characterize the sample.

41. The method of claim 36, wherein illuminating a region of the sample with light comprises illuminating the sample with more than one wavelength of light.

42. A method for characterizing a region of a sample comprising:

illuminating a region of a sample with light in a wavelength range of about 200 to about 800 nm from an illumination fiber;

diffusely reflecting a portion of the light that illuminates the region;

receiving a portion of the diffusely reflected light at a plurality of collection fibers, wherein at least two of the collection fibers are at different distances from the illumination fiber, and wherein the collection fibers are spatially separated by spacers;

combining the portion of diffusely reflected light collected at two or more collection fibers;

characterizing the region based on at least a calculated scattering coefficient of the diffusely reflected light received by each of the collection fibers; and making a diagnosis regarding the region.

43. The method of claim 42, wherein illuminating a region of the sample comprises illuminating the sample with more than one wavelength of light.

44. The method of claim 42, wherein characterizing the region comprises calculating a scattering coefficient from a portion of the diffusely reflected light received from the individual collection fibers.

45. The method of claim 44, wherein making a diagnosis comprises comparing the scattering coefficient to known values for different types of tissue.

46. The method of claim 42, further comprising moving the illumination and collection fibers along the surface of the sample to characterize a plurality of regions of the sample.

* * * * *